(12) United States Patent
Wang et al.

(10) Patent No.: US 11,510,557 B2
(45) Date of Patent: Nov. 29, 2022

(54) ENDOSCOPE SYSTEM AND ENDOSCOPE

(71) Applicant: OLYMPUS CORPORATION, Tokyo (JP)

(72) Inventors: Xiongwei Wang, Hino (JP); Tsukasa Ota, Hachioji (JP); Takuto Yoshinaga, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 260 days.

(21) Appl. No.: 16/855,520

(22) Filed: Apr. 22, 2020

(65) Prior Publication Data
US 2020/0245853 A1    Aug. 6, 2020

Related U.S. Application Data

(63) Continuation of application No. PCT/JP2018/031578, filed on Aug. 27, 2018.

(30) Foreign Application Priority Data

Oct. 31, 2017    (JP) .............................. JP2017-210228

(51) Int. Cl.
*A61B 1/00*    (2006.01)
*A61B 1/012*    (2006.01)
(Continued)

(52) U.S. Cl.
CPC .......... *A61B 1/0125* (2013.01); *A61B 1/0051* (2013.01); *A61B 1/0055* (2013.01); *A61B 1/018* (2013.01)

(58) Field of Classification Search
None
See application file for complete search history.

(56) References Cited

U.S. PATENT DOCUMENTS

3,610,231 A * 10/1971 Takahashi ............ A61B 1/0057
 396/17
4,688,555 A * 8/1987 Wardle ............... A61B 1/00042
 600/149
(Continued)

FOREIGN PATENT DOCUMENTS

JP    H02-291835 A    12/1990
JP    2009-530051 A    8/2009
(Continued)

OTHER PUBLICATIONS

International Search Report dated Oct. 30, 2018 issued in PCT/JP2018/031578.

*Primary Examiner* — Timothy J Neal
(74) *Attorney, Agent, or Firm* — Scully, Scott, Murphy & Presser, P.C.

(57) ABSTRACT

An endoscope system includes a mother endoscope, a baby endoscope and a fixing member. The mother endoscope includes a first insertion section, a first operation section, a treatment instrument insertion channel and an opening. The baby endoscope includes a second insertion section and a second operation section. The first operation section includes a projection portion. The second operation section includes a recess portion that is a recessed face formed such that at least part of the recessed face comes into face contact with a surface of the projection portion. The second operation section is fixed to the first operation section in a state where the recess portion is in contact with the surface of the projection portion.

8 Claims, 5 Drawing Sheets

(51) Int. Cl.
 *A61B 1/005* (2006.01)
 *A61B 1/018* (2006.01)

(56) References Cited

U.S. PATENT DOCUMENTS

| | | | | |
|---|---|---|---|---|
| 4,947,828 | A | | 8/1990 | Carpenter et al. |
| 5,199,417 | A | * | 4/1993 | Muller .................... A61B 1/07 600/920 |
| 2005/0272975 | A1 | * | 12/2005 | McWeeney .............. A61B 6/06 600/172 |
| 2007/0188604 | A1 | * | 8/2007 | Miyamoto ......... A61B 1/00052 348/65 |
| 2011/0099773 | A1 | * | 5/2011 | Golden ................... F16B 2/185 24/457 |
| 2014/0223701 | A1 | * | 8/2014 | Bean ................. A61B 1/00066 24/483 |

FOREIGN PATENT DOCUMENTS

| | | |
|---|---|---|
| JP | 2011-167460 A | 9/2011 |
| JP | 2016-532504 A | 10/2016 |
| WO | WO 2015/026557 A1 | 2/2015 |

\* cited by examiner

ENDOSCOPE SYSTEM AND ENDOSCOPE

CROSS REFERENCE TO RELATED APPLICATION

This application is a continuation application of PCT/JP2018/031578 filed on Aug. 27, 2018 and claims benefit of Japanese Application No. 2017-210228 filed in Japan on Oct. 31, 2017, the entire contents of which are incorporated herein by this reference.

BACKGROUND OF INVENTION

1. Field of the Invention

The present invention relates to an endoscope system including an endoscope and a medical device fixed to an operation section of the endoscope, and an endoscope fixed to an operation section of another endoscope.

2. Description of the Related Art

A mother-baby endoscope system including a mother endoscope and a baby endoscope has recently been put into practical use as an endoscope used for observing and/or treating the inside of the bile duct or the inside of the pancreatic duct. The mother endoscope is an endoscope with a normal size and exemplarily an endoscope for the duodenum. The baby endoscope is a thinner endoscope than the mother endoscope and is inserted into the treatment instrument insertion channel of the mother endoscope.

In observation and/or therapeutics inside the bile duct or inside the pancreatic duct using such a mother-baby endoscope system, the baby endoscope is caused to protrude into the body cavity from the distal end of the mother endoscope, and only the baby endoscope is caused to be selectively inserted into the bile duct or the pancreatic duct from the duodenal papilla with combinations of bending operation, advancing and retracting operation, twisting operation and the like of the baby endoscope, and raising base operation, bending operation, twisting operation, advancing and retracting operation and the like of the mother endoscope.

There can be a case, in the mother-baby endoscope system, where the operation section of the baby endoscope is fixed to the operation section of the mother endoscope such that one person can operate both the mother endoscope and the baby endoscope. For example, Japanese Patent Application Laid-Open Publication No. 2009-530051 discloses an in-vivo visualization system in which a catheter assembly as a baby endoscope is mounted on an endoscope handle as the operation section of a mother endoscope. In the in-vivo visualization system, a strap is connected to a catheter handle as the operation section of the catheter assembly, and the strap is wound on the periphery of the endoscope handle to attach the catheter handle to the endoscope handle.

SUMMARY OF THE INVENTION

An endoscope system according to an aspect of the present invention includes: an endoscope including a first insertion section, a first operation section coupled to the first insertion section, a treatment instrument insertion channel provided inside the first insertion section and the first operation section, and an opening communicating with the treatment instrument insertion channel and provided in the first operation section; a medical device including a second insertion section configured to be inserted into the treatment instrument insertion channel from the opening, and a second operation section coupled to the second insertion section; and a fixing member that fixes the medical device to the endoscope, wherein the first operation section includes a projection portion that is a part of the first operation section except the opening, the second operation section includes a recess portion that is a part of a surface of the second operation section and is a recessed face formed such that at least part of the recessed face comes into face contact with a surface of the projection portion, and the second operation section is fixed to the first operation section in a state where the recess portion is in contact with the surface of the projection portion.

An endoscope according to an aspect of the present invention is an endoscope which is fixed to an operation section of another endoscope, the endoscope including: a bending operation section including a recessed face formed so as to come into face contact with a surface of a projection portion formed on the operation section of the other endoscope; and a fixing member that fixes the bending operation section to the operation section of the other endoscope in a state where the recessed face of the bending operation section is in contact with the surface of the projection portion.

DETAILED DESCRIPTION OF THE PREFERRED EMBODIMENT(S)

Figure 1:
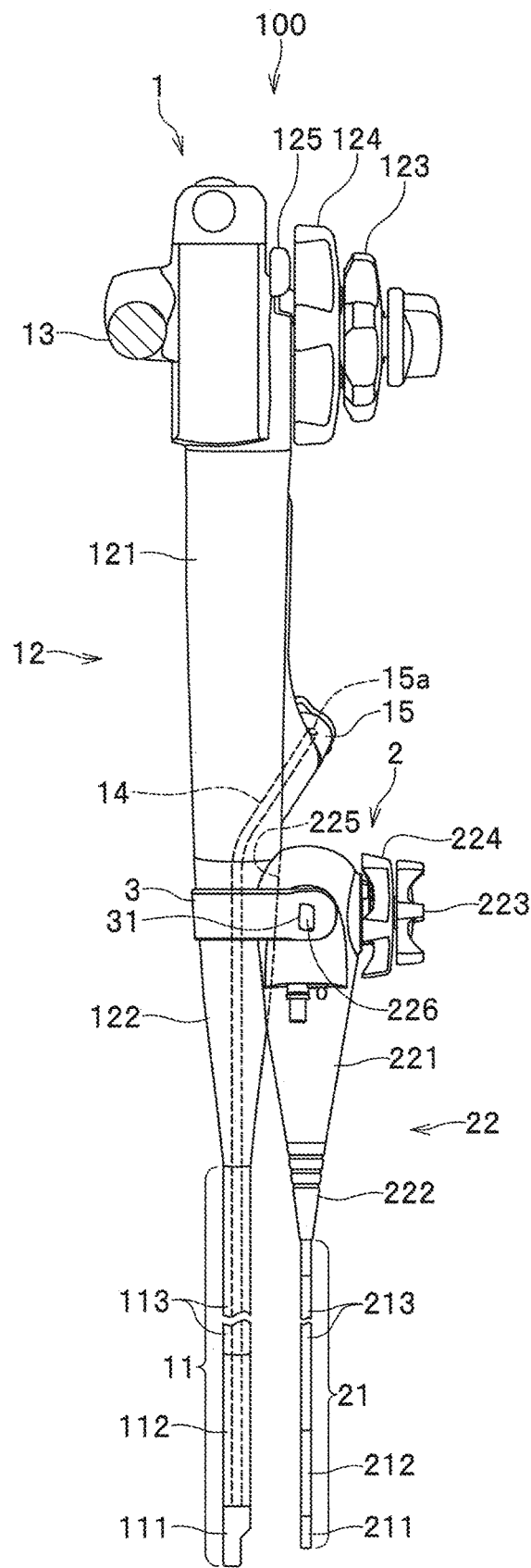
FIG. 1 is an explanatory diagram for explaining a configuration of an endoscope system according to an embodiment of the present invention.

An embodiment of the present invention is described with reference to the drawings.
(Configuration of Endoscope System)

A configuration of an endoscope system according to an embodiment of the present invention is described with reference to FIG. 1. An endoscope system 100 according to the present embodiment is a mother-baby endoscope system including a mother endoscope 1, a baby endoscope 2 as a medical device, and a fixing member 3 for fixing the baby endoscope 2 to the mother endoscope 1.
(Configuration of Mother Endoscope)

A configuration of the mother endoscope 1 is described. The mother endoscope 1 is a side viewing-oblique viewing endoscope, in the present embodiment. The mother endoscope 1 includes a first insertion section 11, and a first operation section 12 coupled to a proximal end of the first insertion section 11.

The first insertion section 11 exemplarily has an elongated shape in which a diameter is about 10 mm and a length is about 1.2 m. The first insertion section 11 includes a distal end portion 111 positioned at a distal end of the first insertion section 11, a bendably configured bending portion 112, and a flexible tubular portion 113 having flexibility. The distal end portion 111, the bending portion 112 and the flexible tubular portion 113 are coupled in an order of the distal end portion 111, the bending portion 112 and the flexible tubular portion 113 from the distal end side of the first insertion section 11. Image pickup means, lighting means, a treatment instrument opening, a treatment instrument raising base and the like, which are not shown in the figure, are provided in the distal end portion 111.

The mother endoscope 1 further includes a treatment instrument insertion channel 14 provided inside the first insertion section 11 and the first operation section 12, and an operation section-side opening (hereinafter expressed simply as opening) 15a which communicates with the treatment instrument insertion channel 14 and is provided in the first operation section 12. The treatment instrument insertion channel 14 also communicates with the treatment instrument opening of the distal end portion 111. A second insertion section of the baby endoscope 2 mentioned later as well as treatment instruments such as forceps is configured to be able to be caused to be inserted into the treatment instrument insertion channel 14. The opening 15a is an opening of a conduit pipe sleeve 15 connected to the first operation section 12, in the present embodiment.

The first operation section 12 includes an operation section body 121. The flexible tubular portion 113 of the first insertion section 11 is connected to the operation section body 121. The first operation section 12 further includes a projection portion 122 which is a part of the first operation section 12 except the opening 15a. The projection portion 122 is coupled to the operation section body 121. The projection portion 122 covers a connection portion of the flexible tubular portion 113 to the operation section body 121, and a vicinity of the connection portion.

The projection portion 122 is used as a bend preventing portion, in the present embodiment. The projection portion 122 namely prevents the flexible tubular portion 113 from unwantedly drastically bending in use of the mother endoscope 1, by covering the aforementioned connection portion of the flexible tubular portion 113 and the vicinity of the connection portion.

The projection portion 122 has a one-directionally long shape. The projection portion 122, and a portion, of the flexible tubular portion 113, that is covered by the projection portion 122 extend in an identical direction. An exterior shape of at least part of the projection portion 122 is a truncated cone shape, in the present embodiment. The exterior shape of the whole projection portion 122 is a truncated cone shape, in the example shown in FIG. 1. A shape of an outer edge of the projection portion 122 in a cross section, of the projection portion 122, perpendicular to a longitudinal direction is a circle. The circle is smaller in diameter as being farther from the operation section body 121.

Note that the exterior shape of the projection portion 122 is not limited to a truncated cone shape but may be a convex polygonal shape such as a truncated pyramid shape or a prism shape, may be a cylinder shape, or may be a shape having any of the truncated cone shape, the convex polygonal shape such as a truncated pyramid shape or a prism shape, and the cylinder shape combined.

The operation section body 121 includes an exterior member configured of a resin. The projection portion 122 is configured of a softer resin than the resin configuring the exterior member.

The first operation section 12 further includes a plurality of first operation members provided in the operation section body 121. The plurality of first operation members are for operating the mother endoscope 1. The plurality of first operation members include two bending operation knobs 123 and 124 for operating bending of the bending portion 112, and a treatment instrument raising lever 125 for operating the treatment instrument raising base provided in the distal end portion 111.

The bending operation knobs 123 and 124 and the treatment instrument raising lever 125 are provided close to an end portion, of the operation section body 121, on an opposite side to the projection portion 122. Note that the conduit pipe sleeve 15 is provided in a portion, of the operation section body 121, between the projection portion 122 and the set of the bending operation knobs 123 and 124 and the treatment instrument raising lever 125.

The mother endoscope 1 further includes a universal cord 13 extending from the first operation section 12. The universal cord 13 is connected to a not-shown endoscope unit for controlling the mother endoscope 1.

(Configuration of Baby Endoscope)

A configuration of the baby endoscope 2 is described. The baby endoscope 2 includes a second insertion section 21, and a second operation section 22 coupled to a proximal end of the second insertion section 21.

The second insertion section 21 exemplarily has an elongated shape in which a diameter is about 3 mm to 4 mm and a length is about 2 m. The second insertion section 21 is inserted into the treatment instrument insertion channel 14 from the opening 15a, and a part of the second insertion section 21 protrudes from the treatment instrument opening provided in the distal end portion 111. The treatment instrument raising base provided in the distal end portion 111 is used for causing the part of the second insertion section 21 protruding from the treatment instrument opening to be raised.

The second insertion section 21 includes a distal end portion 211 positioned at a distal end of the second insertion section 21, a bendably configured bending portion 212, and a flexible tubular portion 213 having flexibility. The distal end portion 211, the bending portion 212 and the flexible tubular portion 213 are coupled in an order of the distal end portion 211, the bending portion 212 and the flexible tubular portion 213 from the distal end side of the second insertion section 21. As shown in FIG. 1, the bending portion 212 is provided close to the distal end of the second insertion section 21. An observation window, a lighting window and the like, which are not shown in the figure, are provided in the distal end portion 211.

The baby endoscope 2 further includes a not-shown channel provided inside the second insertion section 21 and the second operation section 22. The channel communicates with an opening of a pipe sleeve 25 provided in the second operation section 22 and an opening provided in the distal end portion 211. Note that the pipe sleeve 25 is shown in FIG. 2 to FIG. 5 mentioned later.

The second operation section 22 includes an operation section body 221 and a bend preventing portion 222. A flexible tubular portion 213 of the second insertion section 21 is connected to the operation section body 221. The bend preventing portion 222 covers a connection portion of the flexible tubular portion 213 to the operation section body 221 and a vicinity of the connection portion. The bend preventing portion 222 accordingly prevents the flexible tubular portion 213 from unwantedly drastically bending in use of the baby endoscope 2.

The operation section body 221 includes an exterior member configured of a resin. The bend preventing portion 222 is configured of a softer resin than the resin configuring the exterior member.

A not-shown universal cord is connected to the second operation section 22. The universal cord is connected to a not-shown endoscope unit for controlling the baby endoscope 2.

(Configuration of Second Operation Section)

Figure 3:
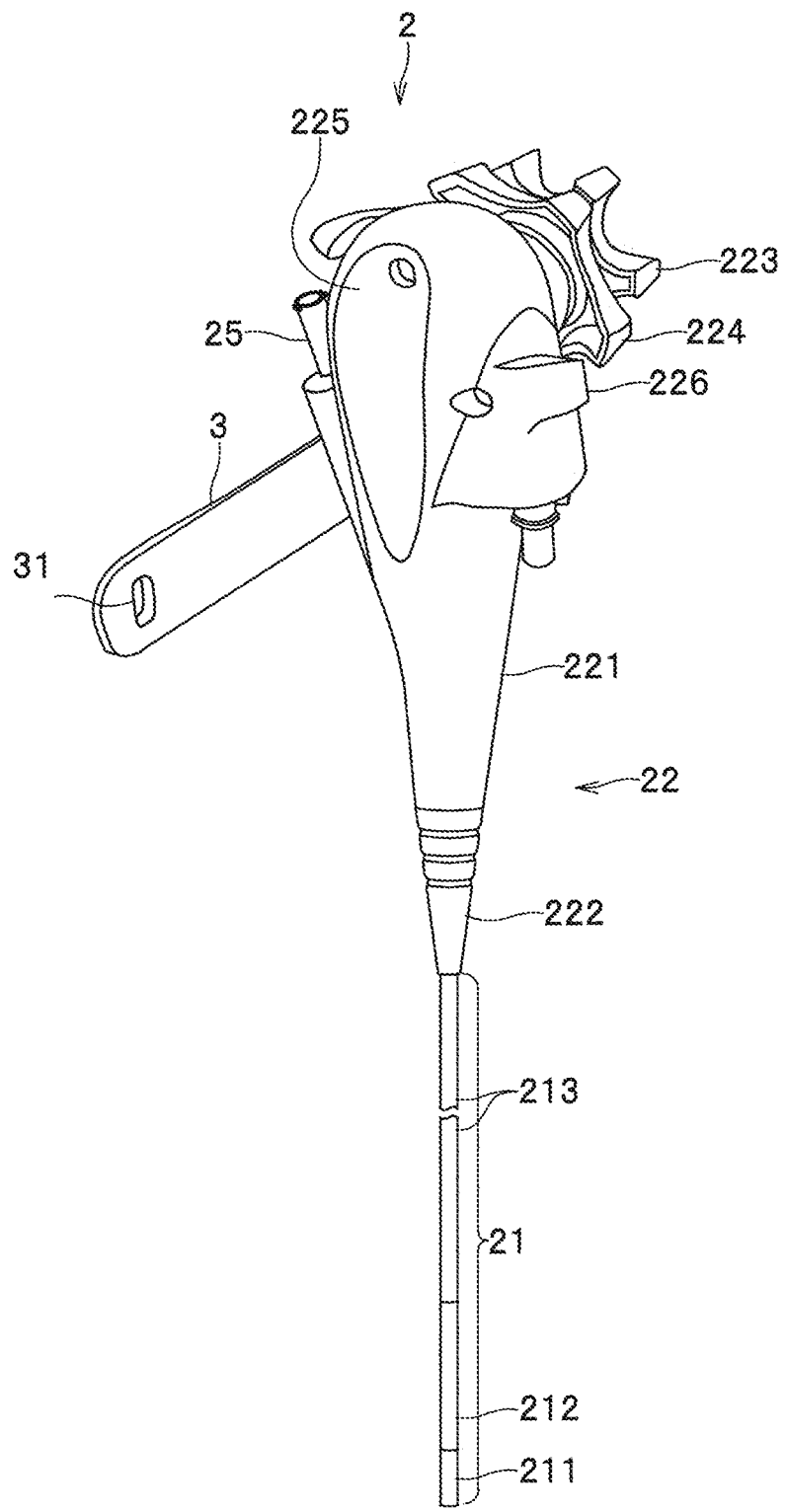
FIG. 3 is a perspective view of a baby endoscope in an embodiment of the present invention.
Figure 4:
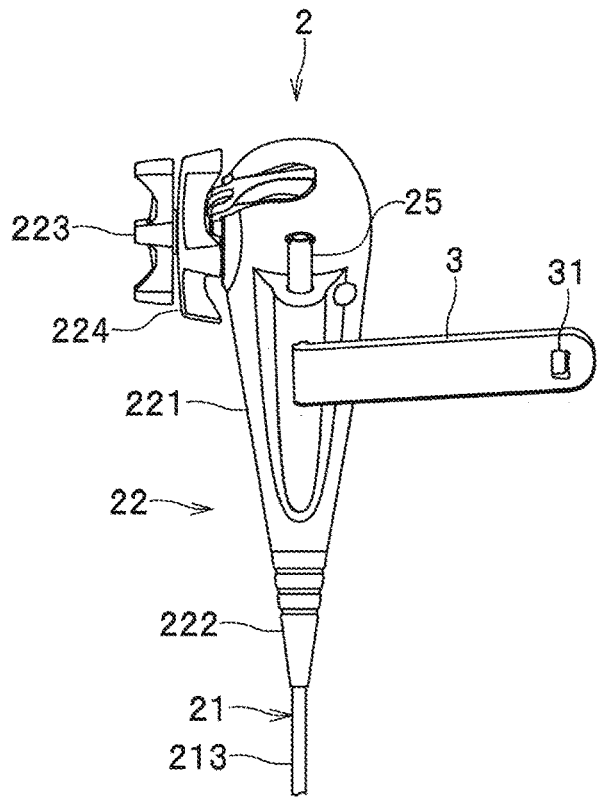
FIG. 4 is a lateral view of a baby endoscope in an embodiment of the present invention.
Figure 5:
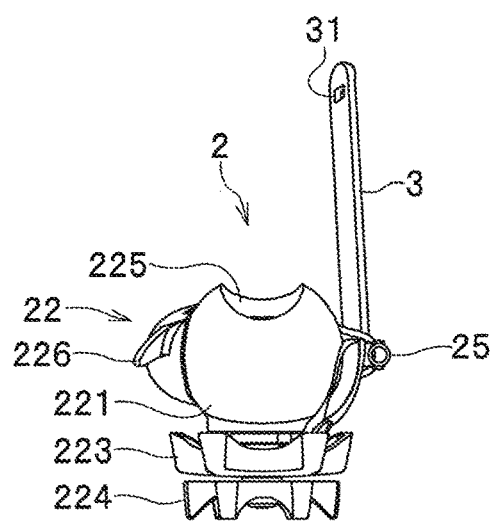
FIG. 5 is a plan view of a baby endoscope in an embodiment of the present invention.

The configuration of the second operation section 22 of the baby endoscope 2 is described more in detail with reference to FIG. 3 to FIG. 5. FIG. 3 is a perspective view of the baby endoscope 2. FIG. 4 is a lateral view of the baby endoscope 2. FIG. 5 is a plan view of the baby endoscope 2.

The second operation section 22 includes a plurality of second operation members provided in the operation section body 221. The plurality of second operation members are for operating the baby endoscope 2. The plurality of second operation members include two bending operation knobs 223 and 224 for operating bending of the bending portion 212 of the second insertion section 21.

As shown in FIG. 3 and FIG. 5, the second operation section 22 further includes a recess portion 225 which is a part of a surface of the operation section body 221 and is a recessed face. Note that since the surface of the operation section body 221 is a part of a surface of the second operation section 22, the recess portion 225 is also a part of the surface of the second operation section 22. As shown in FIG. 3 and FIG. 5, the recess portion 225 is provided on an opposite side to the bending operation knobs 223 and 224 on the surface of the operation section body 221.

As shown in FIG. 4, the fixing member 3 has a belt shape, and one end portion of the fixing member 3 is connected to the operation section body 221. The fixing member 3 includes a locking hole 31 provided close to an opposite end portion to the one end portion of the fixing member 3. The second operation section 22 includes a locking portion 226 which is a protrusion that the locking hole 31 of the fixing member 3 is locked to. The locking portion 226 is provided on the operation section body 221. The fixing member 3 is configured of a resin such as silicone rubber.

(Fixing Method of Baby Endoscope)

A method of fixing the second operation section 22 of the baby endoscope 2 to the first operation section 12 of the mother endoscope 1 is described with reference to FIG. 1 and FIG. 3. As shown in FIG. 1 and FIG. 3, each of the first and second operation sections 12 and 22 has a one-directionally long shape. When the second operation section 22 is fixed to the first operation section 12, first, a direction in which the first insertion section 11 extends and a direction in which the second insertion section 21 extends are made an identical direction to match a longitudinal direction of the second operation section 22 and a longitudinal direction of the first operation section 12. A posture of the second operation section 22 is preferably a posture in which the longitudinal direction of the second operation section 22 is parallel to the longitudinal direction of the first operation section 12.

Next, the recess portion 225 of the second operation section 22 is caused to come into contact with the surface of the projection portion 122 of the first operation section 12 with the posture held. In this state, the second operation section 22 may be adjusted in position such that the bending operation knobs 123 and 124 provided in the first operation section 12 and the bending operation knobs 223 and 224 provided in the second operation section 22 line up along the longitudinal axis of the first operation section 12.

Next, the fixing member 3 is wound on a periphery of the projection portion 122 such that the projection portion 122 is interposed between the second operation section 22 and the fixing member 3. Next, the locking hole 31 of the fixing member 3 is hooked on the locking portion 226 of the second operation section 22. The second operation section 22 is accordingly fixed to the first operation section 12.

The second operation section 22 is fixed to the first operation section 12 as above in a state where the recess portion 225 is in contact with the surface of the projection portion 122. The recess portion 225 is formed such that, at least part of which comes into face contact with the surface of the projection portion 122. The recess portion 225 is formed along the longitudinal axis of the second operation section 22, in the present embodiment.

Figure 6:
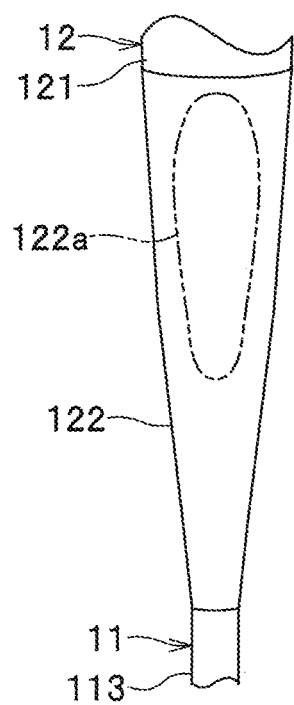
FIG. 6 is a lateral view partially showing a mother endoscope in an embodiment of the present invention.

A shape of the surface of the projection portion 122 is described with reference to FIG. 6. FIG. 6 is a lateral view partially showing the mother endoscope 1. As shown in FIG. 6, the projection portion 122 includes a contacted portion 122a which is a part of the surface of the projection portion 122 and which the recess portion 225 is caused to come into contact with. The contacted portion 122a is a curved face, of the projection portion 122, which protrudes outward, in the present embodiment. To be more specific, the exterior shape of the projection portion 122 is a truncated cone shape, in the present embodiment as mentioned above. The contacted portion 122a accordingly is a curved face configuring a part of a lateral surface of the truncated cone.

The recess portion 225 is a curved face shaped to correspond to the contacted portion 122a, in the present embodiment. The recess portion 225 is a recessed curved face corresponding to the curved face configuring a part of a lateral surface of the truncated cone corresponding to the exterior shape of the projection portion 122, particularly in the present embodiment.

Note that the exterior shape of the projection portion 122 may be a convex polygonal shape such as a truncated pyramid shape or a prism shape as mentioned above. In this case, each of the contacted portion 122a and the recess portion 225 may include at least one flat face.

A fixing position of the second operation section 22 can be caused to change to some extent in the longitudinal direction of the projection portion 122, in the example shown in FIG. 1 and FIG. 3. Indicators may be provided on the projection portion 122 and the second operation section 22 in order to more accurately define the fixing position of the second operation section 22. For example, a plurality of colors may be applied separately on the surface of the projection portion 122, or markers may be provided on the surface of the projection portion 122, more specifically, such that a position of the contacted portion 122a can be made clear on the surface of the projection portion 122.

The baby endoscope 2 may include a linear member such as a string, both ends of which are connected to the second operation section 22 in order to prevent the second operation section 22 from dropping when or after the second operation section 22 is fixed. The linear member is exemplarily configured to be able to be hooked on the conduit pipe sleeve 15 of the first operation section 12 or on a protrusion or the like, for the linear member, that is provided on the first operation section 12.

(Usage of Endoscope System)

Figure 2:
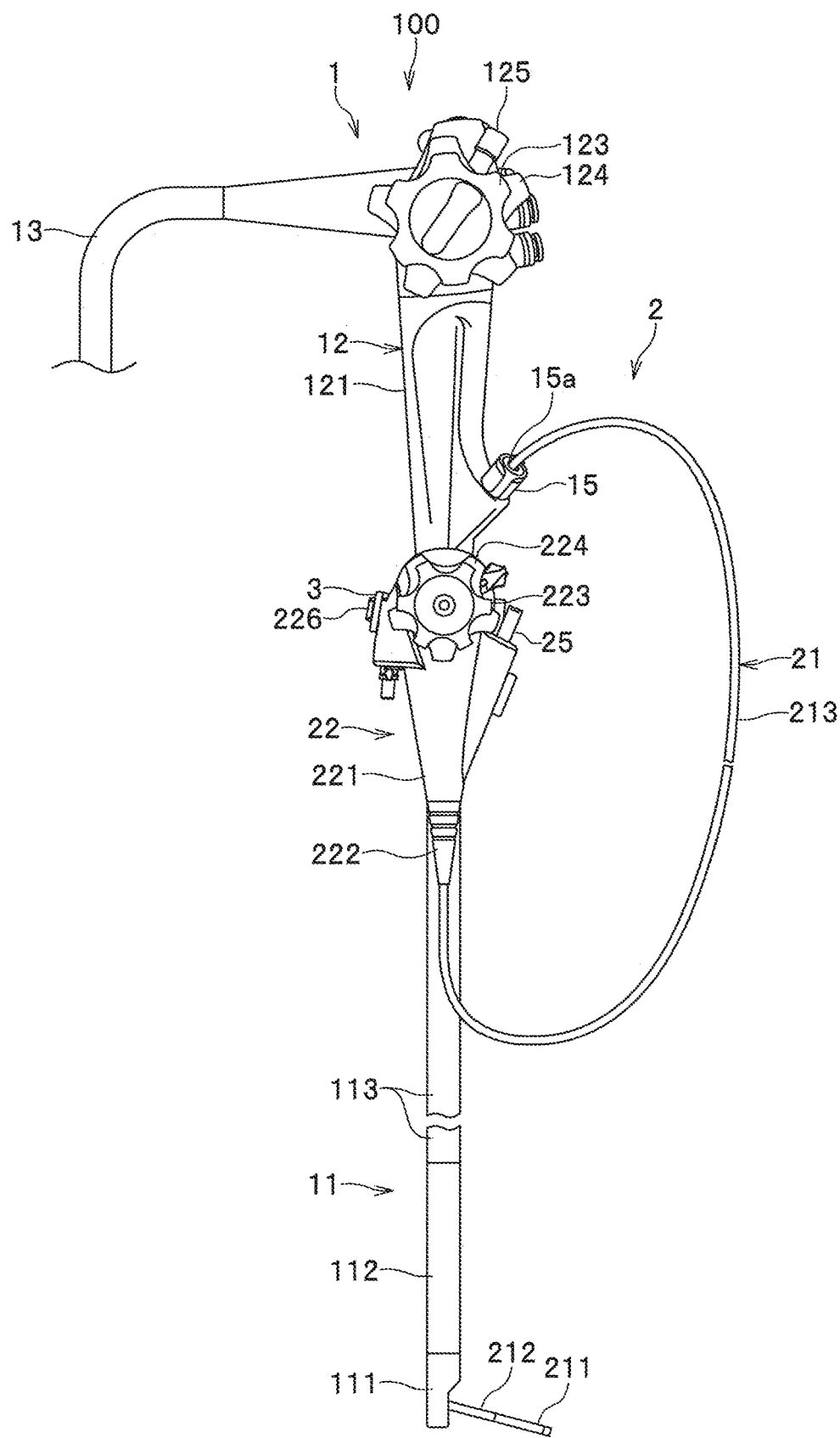
FIG. 2 is an explanatory diagram for explaining a usage of an endoscope system according to an embodiment of the present invention.

A usage of the endoscope system 100 is briefly described with reference to FIG. 1 and FIG. 2. FIG. 2 is an explanatory diagram for explaining a usage of the endoscope system 100. Here is exemplarily described a case where an inside of a bile duct or an inside of a pancreatic duct is observed or treated using the endoscope system 100. First, the second insertion section 21 of the baby endoscope 2 is caused to be inserted into the treatment instrument insertion channel 14 from the opening 15a of the mother endoscope 1. Next, the second insertion section 21 of the baby endoscope 2 is caused to protrude into a body cavity from the treatment instrument opening of the distal end portion 111 of the first insertion section 11 of the mother endoscope 1. Next, the second insertion section 21 is caused to be selectively inserted into the bile duct or the pancreatic duct from a duodenal papilla with combinations of bending operation, advancing and retracting operation, twisting operation and the like of the baby endoscope 2, and raising base operation, bending operation, twisting operation, advancing and retracting operation and the like of the mother endoscope 1. The inside of the bile duct or the inside of the pancreatic duct can accordingly be observed or treated using the baby endoscope 2.

(Operation and Effects of Endoscope System)

Operation and effects of the endoscope system 100 are described. The second operation section 22 of the baby endoscope 2 is fixed to the first operation section 12 of the mother endoscope 1 in the state where the recess portion 225 is in contact with the surface of the projection portion 122, in the present embodiment as mentioned above. Here is supposed an endoscope system of a comparative example in which an operation section, of a baby endoscope, that the recess portion 225 in the present embodiment is not provided on is fixed to an operation section of a mother endoscope. In the comparative example, a portion, of a surface of the operation section of the mother endoscope, which faces the operation section of the baby endoscope is a convex curved face, and a portion, of a surface of the operation section of the baby endoscope, which faces the operation section of the mother endoscope is a flat face or a convex curved face. The operation section of the baby endoscope therefore comes into point contact with the surface of the operation section of the mother endoscope, in the comparative example. Hence, a gap between the operation section of the baby endoscope and the operation section of the mother endoscope results in being large, in the comparative example.

On the contrary, the recess portion 225 is formed such that, at least part of which comes into face contact with the surface of the projection portion 122, in the present embodiment. The contacted portion 122a of the projection portion 122 is the curved face and the recess portion 225 is the curved face shaped to correspond to the contacted portion 122a, particularly in the present embodiment. According to the present embodiment, a contact area of the recess portion 225 with the projection portion 122 can accordingly be made larger than in the comparative example, and as a result, the gap between the second operation section 22 and the first operation section 12 can be made small. According to the present embodiment, frictional resistance between the second operation section 22 and the first operation section 12 can accordingly be made large to prevent a position and/or a posture of the second operation section 22 fixed to the first operation section 12 from being displaced.

The projection portion 122 is configured of a softer resin than the resin configuring the exterior member of the operation section body 121, in the present embodiment. According to the present embodiment, the contact area of the recess portion 225 with the projection portion 122 can accordingly be made larger than in a case where the recess portion 225 is caused to come into contact with the operation section body 121, by causing the recess portion 225 to come into close contact with the projection portion 122.

Note that in view of the fact that frictional resistance between the second operation section 22 and the first operation section 12 can be made large, anti-slip processing or surface processing may be performed on at least one of the recess portion 225 and the projection portion 122.

The recess portion 225 is directly provided on the second operation section 22, in the present embodiment. According to the present embodiment, the second operation section 22 can accordingly be made smaller than in a case where a fixing member corresponding to the recess portion 225 would be provided on the second operation section 22.

The recess portion 225 is shaped to correspond to the contacted portion 122a of the projection portion 122, in the present embodiment. According to the present embodiment, the fixing position of the second operation section 22 can accordingly be easily recognized, and as a result, fixing work of the second operation section 22 can be easily performed.

The second operation section 22 is fixed to the first operation section 12 in a posture in which the longitudinal direction of the second operation section 22 is parallel to the longitudinal direction of the first operation section 12, in the present embodiment. According to the present embodiment, an operation section into which the first operation section 12 and the second operation section 22 are integrated can accordingly be made small. According to the present embodiment, the operation section can accordingly be easily handled.

The present invention is not limited to the aforementioned embodiment but various modifications, alterations and the like can occur without departing from the scope and spirit of the present invention. For example, the projection portion may be a part of the operation section body 121 or may be provided across both on the operation section body 121 and on the bend preventing portion covering the flexible tubular portion 113.

The second operation section 22 may be fixed to the first operation section 12 in a posture in which the longitudinal direction of the second operation section 22 is not parallel to the longitudinal direction of the first operation section 12. The recess portion 225 may namely be formed along an axis different from the longitudinal axis of the second operation section 22.

There may be fixed, to the first operation section 12 of the mother endoscope 1, an operation section of a medical device, other than an endoscope, including an insertion section and an operation section, in place of the baby endoscope 2. Examples of such a medical device include a medical device with an operable catheter or the like as the insertion section.

What is claimed is:

1. An endoscope system comprising:
an endoscope including a first insertion section, a first operation section coupled to the first insertion section, a treatment instrument insertion channel provided inside the first insertion section and the first operation section, and an opening communicating with the treatment instrument insertion channel and provided in the first operation section;
a medical device including a second insertion section configured to be inserted into the treatment instrument insertion channel from the opening, and a second operation section coupled to the second insertion section; and a fixing member that fixes the medical device to the endoscope, wherein the first operation section includes a projection portion that is a part of the first operation section except the opening, the second operation section includes a recess portion that is a part of a surface of the second operation section and is a recessed face formed such that at least part of the recessed face comes into face contact with a surface of the projection portion, and the second operation section is fixed to the first operation section in a state where the recess portion is in contact with the surface of the projection portion.

2. The endoscope system according to claim 1, wherein the projection portion includes a contacted portion that is a part of the surface of the projection portion and the recess portion is caused to come into contact with, the contacted portion is a curved face, of the projection portion, that protrudes outward, and the recess portion is a curved face shaped to correspond to the contacted portion.

3. The endoscope system according to claim 2, wherein an exterior shape of at least part of the projection portion is a truncated cone shape.

4. The endoscope system according to claim 1, wherein the first operation section further includes an operation section body, the first insertion section is connected to the operation section body, and the projection portion is coupled to the operation section body and covers a connection portion of the first insertion section to the operation section body.

5. The endoscope system according to claim 4, wherein the operation section body includes an exterior member configured of a resin, and the projection portion is configured of a softer resin than the resin configuring the exterior member.

6. The endoscope system according to claim 1, wherein each of the first and second operation sections includes a one-directionally long shape, and the second operation section is fixed to the first operation section in a posture in which a longitudinal direction of the second operation section is parallel to a longitudinal direction of the first operation section.

7. The endoscope system according to claim 1, wherein the endoscope is a mother endoscope and the medical device is a baby endoscope.

8. The endoscope system according to claim 7, wherein the second insertion section includes a bending portion provided close to an end portion, of the second insertion section, on an opposite side to the second operation section, the second operation section further includes an operation member configured to operate bending of the bending portion, and the recess portion is provided on an opposite side to the operation member on the surface of the second operation section.

* * * * *